United States Patent
Carrillo, Jr. et al.

(10) Patent No.: US 8,632,522 B2
(45) Date of Patent: *Jan. 21, 2014

(54) CATHETER WITH DIRECTED FLOW DESIGN

(75) Inventors: Oscar R. Carrillo, Jr., Attleboro, MA (US); Russell F. Durgin, Attleboro, MA (US); Sheila L. Caira, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 453 days.

This patent is subject to a terminal disclaimer.

(21) Appl. No.: 12/826,406

(22) Filed: Jun. 29, 2010

(65) Prior Publication Data

US 2010/0268195 A1   Oct. 21, 2010

Related U.S. Application Data

(63) Continuation of application No. 10/953,921, filed on Sep. 29, 2004, now Pat. No. 7,744,585.

(51) Int. Cl.
*A61M 25/00* (2006.01)

(52) U.S. Cl.
USPC ........................................................ 604/523

(58) Field of Classification Search
USPC ........... 604/39, 40, 43, 164.13, 264, 523–528
See application file for complete search history.

(56) References Cited

U.S. PATENT DOCUMENTS

| | | |
|---|---|---|
| 4,279,252 A | 7/1981 | Martin |
| 4,516,972 A | 5/1985 | Samson |
| 4,571,240 A | 2/1986 | Samson et al. |
| 4,601,697 A | 7/1986 | Mammolenti et al. |
| 4,636,346 A | 1/1987 | Gold et al. |
| 4,657,024 A | 4/1987 | Coneys |
| 4,784,638 A | 11/1988 | Ghajar et al. |
| 4,898,591 A | 2/1990 | Jang et al. |
| 4,925,710 A | 5/1990 | Buck et al. |
| 5,078,702 A | 1/1992 | Pomeranz |
| 5,201,723 A | 4/1993 | Quinn |
| 5,221,270 A | 6/1993 | Parker |
| 5,234,416 A | 8/1993 | Macaulay et al. |
| 5,254,107 A | 10/1993 | Soltesz |
| 5,300,048 A | 4/1994 | Drewes, Jr. et al. |
| 5,399,164 A | 3/1995 | Snoke et al. |
| 5,405,329 A | 4/1995 | Durand |
| 5,405,341 A | 4/1995 | Martin |
| 5,441,489 A | 8/1995 | Utsumi et al. |
| 5,445,624 A | 8/1995 | Jimenez |
| 5,480,380 A | 1/1996 | Martin |
| 5,496,292 A | 3/1996 | Burnham |
| 5,531,700 A | 7/1996 | Moore et al. |
| 5,538,513 A | 7/1996 | Okajima |
| 5,542,924 A | 8/1996 | Snoke et al. |
| 5,554,139 A | 9/1996 | Okajima |

(Continued)

*Primary Examiner* — Matthew F DeSanto

(74) *Attorney, Agent, or Firm* — Seager, Tufte & Wickhem LLC

(57) ABSTRACT

A catheter includes an elongated catheter body having a proximal portion and a distal portion. A first longitudinally accessible lumen and a second lumen extend side by side within and along the proximal portion, and the first lumen and the second lumen form a single common lumen within the distal portion which extends to a distal end of the distal portion. The first lumen and second lumen are co-axial within the distal portion prior to forming a single common lumen.

18 Claims, 3 Drawing Sheets

(56) References Cited

U.S. PATENT DOCUMENTS

| | | |
|---|---|---|
| 5,571,093 A | 11/1996 | Cruz et al. |
| 5,584,821 A | 12/1996 | Hobbs et al. |
| 5,624,392 A | 4/1997 | Saab |
| 5,662,622 A | 9/1997 | Gore et al. |
| 6,027,474 A * | 2/2000 | Douk et al. ............... 604/95.01 |
| 6,306,074 B1 * | 10/2001 | Waksman et al. ............... 600/7 |
| 6,346,093 B1 * | 2/2002 | Allman et al. ............ 604/167.06 |
| 6,579,300 B2 | 6/2003 | Griego et al. |
| 6,893,417 B2 | 5/2005 | Gribbons et al. |
| 7,744,585 B2 * | 6/2010 | Carrillo et al. ............... 604/523 |
| 2003/0088153 A1 | 5/2003 | Carrillo, Jr. et al. |
| 2004/0068250 A1 | 4/2004 | Boutilette et al. |

\* cited by examiner

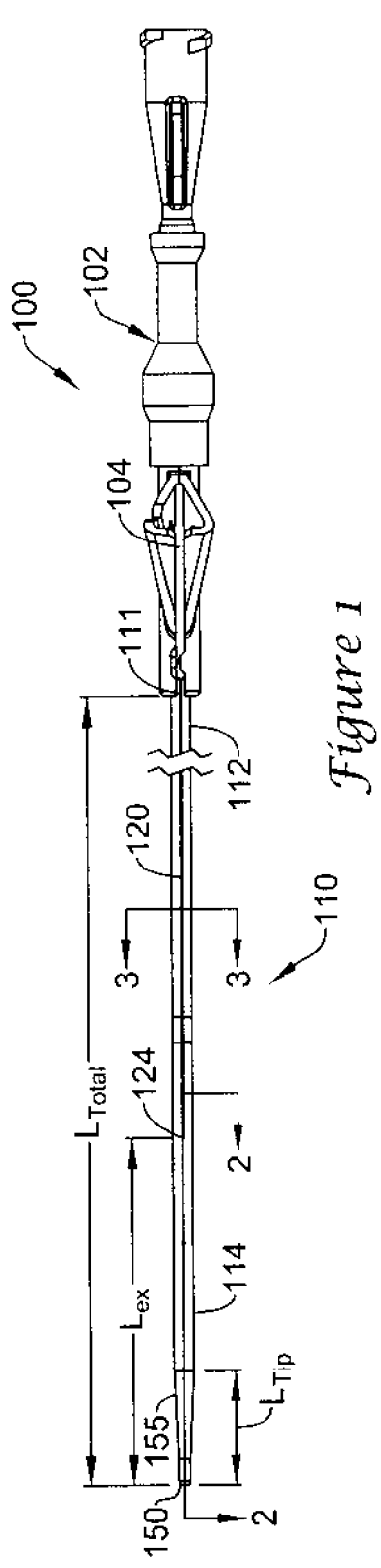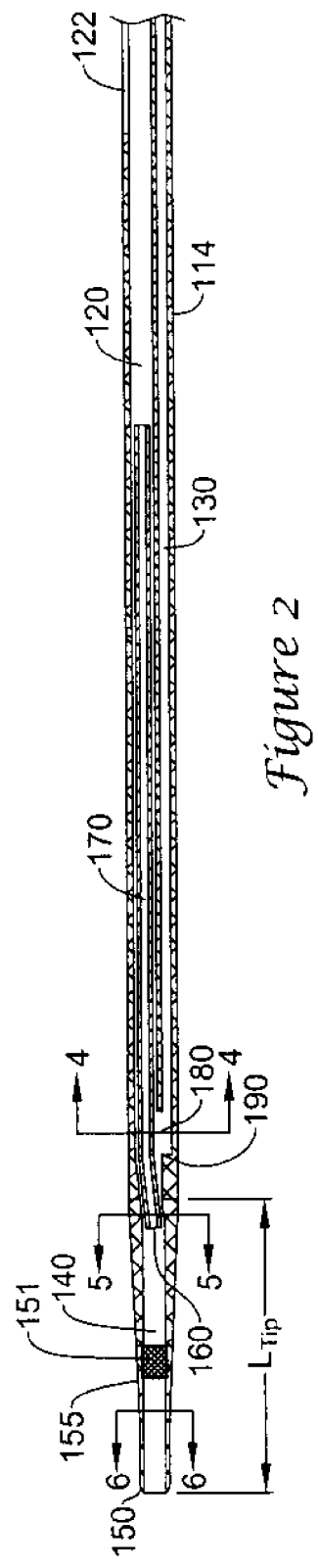

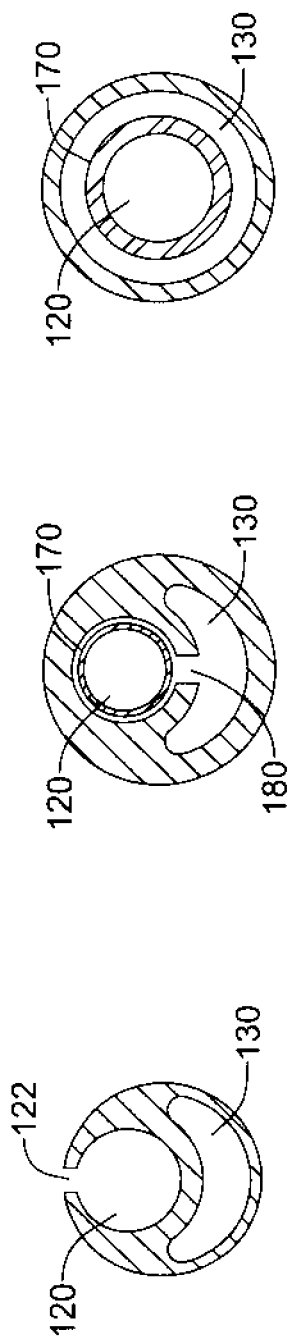

CATHETER WITH DIRECTED FLOW DESIGN

RELATED APPLICATIONS

This application is a continuation of co-pending U.S. application Ser. No. 10/953,921, filed Sep. 29, 2004, the entire disclosure of which is incorporated herein by reference.

FIELD OF THE INVENTION

The invention relates generally to a catheter useful in performing diagnostic and/or therapeutic modalities in the biliary tree.

BACKGROUND

Endoscopic procedures for treating abnormal pathologies within the alimentary canal system and biliary tree (including the biliary, hepatic and pancreatic ducts) are increasing in number. The endoscope provides access to the general area of a desired duct using direct visualization. However, the duct itself must be navigated using a catheter in conjunction with fluoroscopy and guidewires.

If visualization of the common bile duct is desired, the guidewire can be guided into the common bile duct and the catheter advanced over the guidewire until the distal end thereof is positioned at a desired location for delivery of contrast media for fluoroscopic visualization of the anatomical detail within the common bile duct.

Visualization may reveal selected areas within the common bile duct that require treatment. To treat the selected areas, a different catheter is typically required, necessitating a catheter exchange. A catheter exchange typically involves removing the first catheter from the endoscope, over the guide wire, and advancing a second catheter over the guidewire to the desired treatment site. Once the guidewire is in place relative to the targeted area, it is highly desirable to maintain the position of the guidewire during subsequent catheter procedures, including during a catheter exchange procedure. If the guidewire moves during such a procedure, the guidewire may need to be re-directed through the body ducts to the target site, which is often a difficult and time consuming task.

Single and multi-lumen extrusions are currently used to manufacture catheters. Each lumen is intended to perform a specific function (i.e., injection of contrast media, delivery of guide wire, etc.). The increasing number of lumens has added functionality to catheter design. However, the catheter diameter requirements have remained the same, and this means that the same area has to be broken down into a greater number of smaller sections. This reduction in the size of each lumen has put limits on the performance of each lumen for certain applications.

SUMMARY OF SOME EMBODIMENTS

The invention generally relates to a catheter useful in performing diagnostic and/or therapeutic modalities in the biliary tree. At least some embodiments include a catheter having a first and second lumen merging into a single common lumen near the distal end of the catheter. In some embodiments, the first and the second lumen are side-by-side in a proximal portion of the catheter and coaxial in a distal portion of the catheter. In some embodiments, a restriction is present in a fluid infusion lumen near the distal end of the catheter sufficient to increase a velocity of fluid flowing out of the distal end.

In one illustrative embodiment, a catheter includes an elongated catheter body having a proximal portion and a distal portion. A first longitudinally accessible lumen and a second lumen extend side-by-side within and along the proximal portion, and the first lumen and the second lumen form a single common lumen within the distal portion which extends to a distal end of the distal portion. The first lumen and second lumen are co-axial within the distal portion prior to forming a single common lumen.

In another illustrative embodiment, a catheter includes an elongated catheter body having a proximal portion and a distal portion. A first lumen having a first cross-sectional area and a second lumen having a second cross-sectional area extend side-by-side within and along the proximal portion. The first lumen and the second lumen form a single common lumen within the distal portion which extends to a distal end of the distal portion. Proximal of the single common lumen, the second lumen comprises a restriction having a third cross-sectional opening area being in a range of about 10 to about 75% of the second cross-sectional area.

In another embodiment, a catheter includes an elongated catheter body having a proximal portion and a distal portion. A first lumen and a second lumen extend side-by-side within and along the proximal portion, and the first lumen and the second lumen form a single common lumen within the distal portion which extends through a tapered distal end of the distal portion. The first lumen and second lumen form a single common lumen within the distal portion, and the first lumen terminates with an open end within the tapered distal end.

BRIEF DESCRIPTION OF THE DRAWINGS

The invention may be more completely understood in consideration of the following detailed description of various embodiments of the invention in connection with the accompanying drawings, in which:

FIG. 1 is a plan view of an illustrative catheter;

FIG. 2 is a longitudinal cross-sectional view of a portion of the illustrative catheter of FIG. 1 taken along line 2-2;

FIGS. 3 to 6 are cross-sectional views of the illustrative catheter of FIGS. 1 and 2 taken along line 3-3 to line 6-6, respectively;

FIG. 7 is a cross-sectional view of another illustrative catheter;

DETAILED DESCRIPTION

Figure 8:
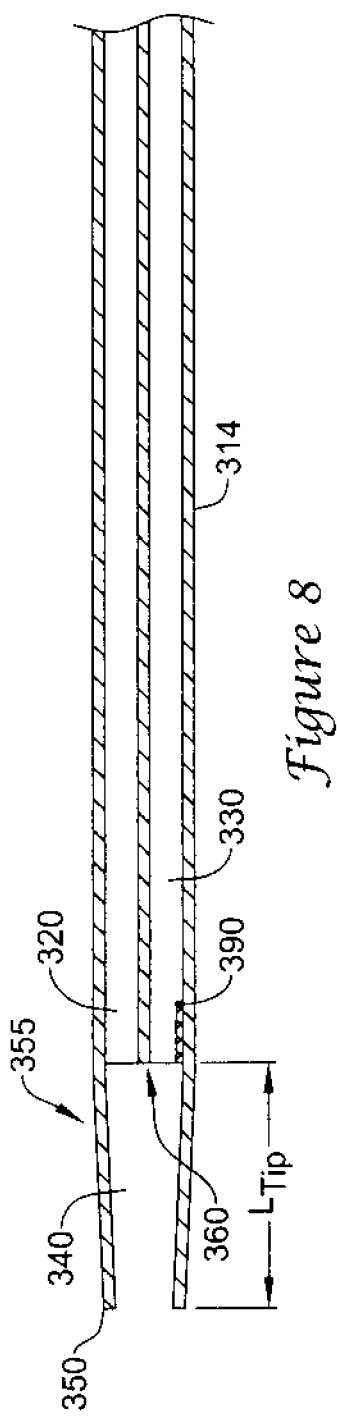
FIG. 8 is a cross-sectional side view of another illustrative catheter of FIG. 1 taken along line 2-2.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials may be illustrated for the various elements, those skilled in the art will recognize that many of the examples provided have suitable alternatives that may be utilized.

Unless otherwise indicated, all numbers expressing numerical amounts, quantities of ingredients, and so forth used in the specification and claims are to be understood as being modified in all instances by the term "about". Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The Figures show exemplary embodiments of a catheter according to the present invention. The catheter can be used in catheter procedures for accessing targeted anatomical regions through, for example, the alimentary canal. In some embodiments, the present invention incorporates features that allow rapid exchange of a catheter by a single operator. The catheter of the present invention can allow shorter length guidewires to be used, resulting in procedures which require less medical personnel, are less time consuming, or less costly. Additionally, the present invention is adaptable to a variety of catheter devices used for catheter procedures within the alimentary canal or any other body lumen.

One illustrative diagnostic technique utilizing a catheter of the present invention is Endoscopic Retrograde Cholangiopancreatography (ERCP). The ERCP technique is an endoscopic technique which involves the placement of a side-viewing instrument within the descending duodenum. The procedure eliminates the need for invasive surgical procedures for identifying biliary stones and other obstructions of the biliary and pancreatic ducts. Utilizing this technique, the Papilla of Vater and common biliary duct are cannulated, contrast medium injected, and the pancreatic ducts and the hepatobiliary tree visualized radiographically or examined with a duodena fiberscope. Skilled medical practitioners can visualize approximately 90-95% of the biliary and pancreatic ducts using this technique. ERCP is typically performed on an X-ray table. During the procedure, the patient's oropharynx is anesthetized with topical lidocaine, and the patient is sedated intravenously with diazepam. Atropine and glucagon are given intravenously to relax the duodenal muscles. To summarize the procedure, an ERCP catheter is initially inserted through the endoscope and into the biliary or pancreatic ducts. A radio-opaque contrast medium is then injected through the lumen of the catheter in order to identify obstructions such as bile stones. Once located and identified, such stones can then be eliminated or destroyed by methods such as mechanical lithotripsy.

The invention generally relates to a catheter useful in performing diagnostic and/or therapeutic modalities in the biliary tree. At least some embodiments include a catheter having a first and a second lumen merging into a single common lumen near the distal end of the catheter. In some embodiments, the first and second lumen are side-by-side in a proximal portion of the catheter and coaxial in a distal portion of the catheter. In some embodiments, a restriction is present in a fluid infusion lumen near the distal end of the catheter sufficient to increase a velocity of fluid flowing out of the distal end. While the invention is not so limited, an appreciation of various aspects of the invention will be gained through a discussion of the various illustrative embodiments and examples provided below.

Referring to FIG. 1, a plan view of an illustrative catheter 100 is shown. The catheter 100 includes an illustrative hub 102 connected to a proximal end 111 of an elongated catheter body 110. The hub 102 can include a guidewire introducer 104. The elongated catheter body 110 includes a proximal portion 112 and a distal portion 114. The proximal portion 112 can have a first cross-sectional diameter, and the distal portion 114 can have a second cross-sectional diameter that can be smaller than the first cross-sectional diameter. The elongated catheter body 110 can include two or more lumens extending along at least a portion of the elongated catheter body 110 length $L_{total}$. The elongated catheter body 110 length $L_{total}$ can extend from the proximal end 111 to a catheter distal end 150. In illustrative embodiments, the elongated catheter body 110 length $L_{total}$ can be in a range of about 100 to about 300 cm, or about 150 to about 250 cm, or about 175 to about 225 cm, or about 200 cm.

Elongate catheter body 110 may be sized for slidable passage through the lumen of an endoscope (not shown). Elongate catheter body 110 can be formed by an extrusion process. Elongate catheter body 110 may be formed of an extruded polymeric material. In one embodiment, the polymeric material can be polytetrafluoroethylene, polyether block amide, nylon or a combination or blend of these. Elongate catheter body 110 can have a varying flexibility along its length. For example, the proximal portion 112 can be less flexible than the distal portion. The flexibility can be varied by selection of material along the elongate catheter body 110 length and/or by adding to reducing any layers forming the elongate catheter body 110. Catheters which are contemplated include, but are not limited to, cannulas, sphincterotomes, cytology devices, and devices for stone retrieval and stent placement.

In some embodiments, the elongated catheter body 110 can include a first lumen 120 which is laterally accessible to allow the catheter 100 to operate as a rapid exchange or single operator exchange catheter. The term "laterally accessible lumen" is defined herein to refer to a lumen that can be accessed along its length and includes lumens that have a C-shaped profile, a U-shaped, a closed lumen having a longitudinal area of perforations or weakness to allow a user to longitudinally open the lumen, and the like. FIG. 3 is a cross-sectional view of the catheter 100 taken along line 3-3. This Figure shows an illustrative side-by-side two lumen construction where the first lumen 120 has an open channel 122 (C-shaped) that allows a guidewire to move laterally from the first lumen 120 to a position exterior of the first lumen 120. Referring back to FIG. 1, at least a portion of the first lumen 120 is closed forming an exchange length $L_{ex}$ that extends from a distal guidewire port 124 to the distal end 150. In illustrative embodiments, the exchange length $L_{ex}$ can be in a range of about 1 to about 30 cm, or about 2 to about 10 cm, or about 3 to about 8 cm, or about 4 to about 6 cm.

In some embodiments, the elongate catheter body 110 includes a distal taper 155 which tapers to distal end 150. Additionally, the distal portion 114 can include high contrast, or color coded distal markers 151. At least portions of the distal portion 114 can be radiopaque for fluoroscopic visualization of the distal taper 155 region during a catheter procedure.

FIG. 2 is a longitudinal cross-sectional view of a portion of the illustrative catheter 100 taken along line 2-2. This Figure shows the distal portion 114 of the elongated catheter body 110. In this illustrative embodiment, at least a first lumen 120 and a second lumen 130 extend side-by-side within the proximal portion 112 and a portion of the distal portion 114 of the elongated catheter body 110. The first lumen 120 and the second lumen 130 merge near the distal end 150 forming a common distal lumen 140 within a portion of the distal portion 114. The common distal lumen 140 extends to the distal end 150 of the distal portion 114. In one illustrative embodiment, the distal portion 114 includes a tapered distal tip 155 having a tip length $L_{tip}$ that extends from a point where the tip begins to reduce in diameter to the distal end 150. The tip length $L_{tip}$ can be in a range of about 0.1 to about 5%, or about 0.2 to about 1%, or about 0.2 to about 0.75% of the elongated catheter body 110 length $L_{total}$. In an illustrative embodiment, the tip length $L_{tip}$ can be in a range of about 1 to about 30 cm, or about 2 to about 10 cm, or about 3 to about 8 cm, or about 5 cm. In another illustrative embodiment, the tip length $L_{tip}$ can be in a range of about 1 to about 30 cm, or about 5 to about 20 cm, or about 10 to about 15 cm, or about 13 cm.

Formation of the single common lumen 140 can be accomplished in a variety of ways. In an illustrative embodiment, single common lumen 140 begins as a lumen transition 180 where the second lumen 130 forms around the first lumen 120. This illustrative embodiment is shown in FIG. 4 which is taken along the line 4-4 of FIG. 2. FIG. 5 is taken along line 5-5 of FIG. 2. FIG. 5 shows the first lumen 120 within the second lumen 130 in a co-axial arrangement within the distal portion 114 of the elongated catheter body 110. In some embodiments, the first lumen 120 ends or terminates as an open end 160 proximal of the distal end 150. The first lumen 120 can end or terminate as an open end 160 within the tapered distal tip 155. The first lumen 120 can be in fluid communication with the second lumen 130 and the single common lumen 140 at the first lumen open end 160. The single common lumen 140 can begin at the first lumen open end 160. FIG. 6 is taken along line 6-6 of FIG. 2. FIG. 6 shows a single common lumen 140. In an illustrative embodiment, the single common lumen 140 distal end 150 can have an inside cross-sectional diameter in the range of about 0.75 to about 1.25 mm or about 1 mm. In illustrative embodiments, the first lumen open end 160 is less than about 20, 15, 10, 5, 4, 3, 2 or 1 mm from the distal end 150. In other illustrative embodiments, the first lumen open end 160 can be about 1 to about 15 mm, or about 1 to about 10 mm, or about 1 to about 5 mm, or about 5 to about 10 mm from the distal end 150.

The first lumen 120 can have a first cross-sectional area. The second lumen 130 can have a second cross-sectional area. In at least some embodiments, the second lumen 130 can have a restriction 190 that reduces the second lumen 130 second cross-sectional area. This restriction 190 can provide an opening having a third cross-sectional area that is less than the second cross-sectional area. If fluid is provided through the second lumen 130 at a constant pressure, the restriction 190 can increase the velocity of the fluid through the restriction 190 opening. This increased fluid velocity into the single common lumen 140 near the distal end 150 aids in minimizing fluid flow back into the first lumen 120. In illustrative embodiments the restriction 190 opening third cross-sectional area can be in a range of about 10 to about 75%, or about 25 to about 50% of the second lumen 130 second cross-sectional area proximal the restriction. In some embodiments, the single common lumen 140 can have a fourth cross-sectional area that is greater than the second lumen 130 second cross-sectional area.

The first lumen 120 can include a tube 170 that extends across the lumen transition 180. This tube 170 can be formed of any material and can be integral with the first lumen 120 proximal of the lumen transition 180. The tube 170 can also be thin-walled and inserted within lumen 120 and affixed thereto. In one embodiment, the tube 170 is formed of a polyimide material, is sized to accept a guide wire, and can be about 5 to about 30 cm in length. The tube 170 can be fixed to the first lumen 120 with an adhesive, for example. The tube 170 can be rigid enough such that the tube does not collapse when injection fluid applies pressure around the tube 170 during operation.

The first lumen 120 can be a guidewire lumen. In an illustrative embodiment, the guidewire lumen 120 extends longitudinally between proximal portion 112 and distal end 150 of the elongate catheter body 110. Further, guidewire lumen 120 is sized to receive a guide wire. Guidewire lumen 120 may be a tubular member which is extruded integral with the elongate catheter body 110, or alternatively, the guidewire lumen 120 may be a separate tubular member which is coupled to elongate catheter body 110. It is recognized that guidewire lumen 120 may be formed anywhere along the elongate catheter body 110, may be an extension of the elongate catheter body 110 coupled to distal end 150, or guidewire lumen 120 may run the entire length of the elongate catheter body 110.

The second lumen 130 can be an ancillary lumen. The ancillary lumen 130 can be an injection lumen, allowing for high contrast media flow capability for bubble-free opacification and for excellent visualization of a desired anatomical region. Additionally or alternatively, ancillary lumen 130 may be used for or as part of other ancillary devices, such as a cutting wire lumen or a retrieval balloon lumen.

FIG. 7 is a cross-sectional view of another illustration catheter embodiment. In this embodiment, three lumens 220, 230, 231 extend side-by-side along at least a portion of the distal portion 214. A guidewire lumen 220, an injection lumen 230, and an ancillary lumen 231 are shown. The ancillary lumen 231 may be used for or as part of another ancillary device, such as a cutting wire lumen, or a balloon inflation lumen, as desired.

FIG. 8 is a cross-sectional side view of another illustrative catheter embodiment taken along line 2-2 of FIG. 2. This Figure shows the distal portion 314 of the elongated catheter body. In this illustrative embodiment, at least a first lumen 320 and a second lumen 330 extend side-by-side within the proximal portion and distal portion 314 of the elongated catheter body. The first lumen 320 and the second lumen 330 merge near the distal end 350 forming a common distal lumen 340 within the distal portion 314. The common distal lumen 340 extends to the distal end 350 of the distal portion 314. In one illustrative embodiment, the distal portion 314 includes a tapered distal tip 355 having a tip length $L_{tip}$ that extends from a point where the tip begins to reduce in diameter to the distal end 350. The tip length $L_{tip}$ can be in a range of about 0.1 to about 5%, or about 0.2 to about 1%, or about 0.2 to about 0.75% of the elongated catheter body length $L_{total}$. In an illustrative embodiment, the tip length $L_{tip}$ can be in a range of about 1 to about 30 cm, or about 2 to about 10 cm, or about 3 to about 8 cm, or about 5 cm. In another illustrative embodiment, the tip length $L_{tip}$ can be in a range of about 1 to about 30 cm, or about 5 to about 20 cm, or about 10 to about 15 cm, or about 13 cm.

Formation of the single common lumen 340 can be accomplished in a variety of ways. In the illustrative embodiment, a single common lumen 340 begins as both lumens 320, 330 terminate with open ends. In this embodiment, the first lumen 320 and the second lumen 330 end or terminate as open ends 360 proximal of the distal end 350. The first lumen 320 can end or terminate as an open end 360 within the tapered distal tip 355. The second lumen 330 can end or terminate as an open end 360 within the tapered distal tip 355. In illustrative embodiments, the first lumen 320 and the second lumen 330 terminate at about the same location merging into a single common lumen 340. In other illustrative embodiments, the first lumen 320 and the second lumen 330 can terminate at different locations, then the lumen open end 360 closest to the distal end 350 merges into a single common lumen 340. The first lumen 320 can be in fluid communication with the second lumen 330 and the single common lumen 340 at the lumen open end 360. In an illustrative embodiment, the single common lumen 340 distal end 350 can have an inside diameter in the range of about 0.75 to about 1.25 mm, or about 1 mm. In illustrative embodiments, the first lumen or second lumen open end 360 can be not more than about 20, 15, 10, 5, 4, 3, 2 or 1 mm from the distal end 350. In other illustrative embodiments, the first lumen or second lumen open end 360 can be about 1 to about 15 mm, or about 1 to about 10 mm, or about 1 to about 5 mm, or about 5 to about 10 mm from the distal end 350.

The first lumen 320 can have a first cross-sectional area. The second lumen 330 can have a second cross-sectional area. In at least some embodiments, the second lumen 330 can have a restriction 390 that reduces the second lumen 330 second cross-sectional area. This restriction 390 can provide an opening having a third cross-sectional area that is less than the second cross-sectional area. If fluid is provided through the second lumen 330 at a constant pressure, the restriction 390 can increase the velocity of the fluid through the restriction 390 opening. This increased fluid velocity into the single common lumen 340 near the distal end 350 aids in minimizing fluid flow back into the first lumen 320. In illustrative embodiments the restriction 390 opening third cross-sectional area can be in a range of about 10 to about 75%, or about 25 to about 50% of the second lumen 330 second cross-sectional area proximal the restriction. In some embodiments, the single common lumen 340 can have a fourth cross-sectional area that is greater than the second lumen 330 second cross-sectional area.

Figure 9:
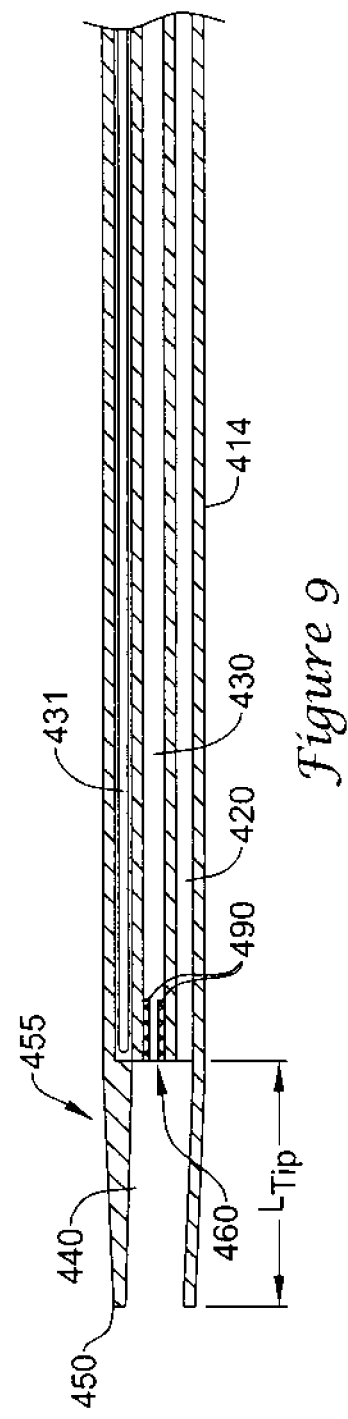
FIG. 9 is a cross-sectional side view of another illustrative catheter of FIG. 1 taken along line 2-2.

FIG. 9 is a cross-sectional side view of another illustrative catheter embodiment taken along line 2-2 of FIG. 1. This Figure shows the distal portion 414 of the elongated catheter body. In this illustrative embodiment, at least a first lumen 420, a second lumen 430, and a third lumen 431 extend side-by-side within the proximal portion and distal portion 414 of the elongated catheter body. The third lumen 431 can be an ancillary lumen 431. The ancillary lumen 431 can be used for or as part of other ancillary devices, such as a cutting wire lumen, a balloon inflation lumen, or a retrieval balloon lumen. It is understood that the catheters described herein can include more or less lumens, as desired. An illustrative sphincterotome device utilizing a cutting wire lumen is disclosed in U.S. Pat. No. 6,579,300, incorporated by reference herein.

The first lumen 420 and the second lumen 430 merge near the distal end 450 forming a common distal lumen 440 within the distal portion 414. The common distal lumen 440 extends to the distal end 450 of the distal portion 414. In one illustrative embodiment, the distal portion 414 includes a tapered distal tip 455 having a tip length $L_{tip}$ that extends from a point where the tip begins to reduce in diameter to the distal end 450. The tip length $L_{tip}$ can be in a range of about 0.1 to about 5%, or about 0.2 to about 1%, or about 0.2 to about 0.75% of the elongated catheter body length $L_{total}$. In an illustrative embodiment, the tip length $L_{tip}$ can be in a range of about 1 to about 30 cm, or about 2 to about 10 cm, or about 3 to about 8 cm, or about 5 cm. In another illustrative embodiment, the tip length $L_{tip}$ can be in a range of about 1 to about 30 cm, or about 5 to about 20 cm, or about 10 to about 15 cm, or about 13 cm.

Formation of the single common lumen 440 can be accomplished in a variety of ways. In the illustrative embodiment, a single common lumen 440 begins as both lumens 420, 430 terminate with open ends 460. In this embodiment, the first lumen 420 and the second lumen 430 end or terminate as open ends 460 proximal of the distal end 450. The first lumen 420 can end or terminate as an open end 460 within the tapered distal tip 455. The second lumen 430 can end or terminate as an open end 460 within the tapered distal tip 455. In illustrative embodiments, the first lumen 420 and the second lumen 430 terminate at about the same location merging into a single common lumen 440. In other illustrative embodiments, the first lumen 420 and the second lumen 430 can terminate at different locations, then the lumen open end 460 closest to the distal end 450 merges into a single common lumen 440. The first lumen 420 can be in fluid communication with the second lumen 430 and the single common lumen 440 at the lumen open end 460. In an illustrative embodiment, the single common lumen 440 distal end 450 can have an inside diameter in the range of about 0.75 to about 1.25 mm or about 1 mm. In illustrative embodiments, the first lumen or second lumen open end 460 can be not more than about 20, 15, 10, 5, 4, 3, 2 or 1 mm from the distal end 450. In other illustrative embodiments, the first lumen or second lumen open end 460 can be about 1 to about 15 mm, or about 1 to about 10 mm, or about 1 to about 5 mm, or about 5 to about 10 mm from the distal end 450.

The first lumen 420 can have a first cross-sectional area. The second lumen 430 can have a second cross-sectional area. In at least some embodiments, the second lumen 430 can have a restriction 490 that reduces the second lumen 430 second cross-sectional area. This restriction 490 can provide an opening having a third cross-sectional area that is less than the second cross-sectional area. If fluid is provided through the second lumen 430 at a constant pressure, the restriction 490 can increase the velocity of the fluid through the restriction 490 opening. This increased fluid velocity into the single common lumen 440 near the distal end 450 aids in minimizing fluid flow back into the first lumen 420. In illustrative embodiments the restriction 490 opening third cross-sectional area can be in a range of about 10 to about 75%, or about 25 to about 50% of the second lumen 430 second cross-sectional area proximal the restriction. In some embodiments, the single common lumen 440 can have a fourth cross-sectional area that is greater than the second lumen 430 second cross-sectional area.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. A medical device comprising:
   an elongate tubular member having a proximal portion with a proximal end and having a distal portion with a distal end, the elongate tubular member including a first lumen extending distally from the proximal end and a second lumen extending distally from the proximal end and disposed side-by-side with the first lumen along the proximal portion, the first lumen being laterally accessible along at least a portion of the length thereof; and a second tubular member disposed within at least a portion of the first lumen, the second tubular member having a curved distal region;
wherein the first lumen and second lumen form a single common lumen having an open distal end within the distal portion of the elongate tubular member.

2. The medical device of claim 1, wherein a proximal end of the second lumen has a first cross-sectional area and a distal end of the second lumen has a second cross-sectional area.

3. The medical device of claim 2, wherein the second cross-sectional area is smaller than the first cross-sectional area.

4. The catheter according to claim 3, wherein the second cross-sectional area is in a range of about 10 to about 75% of the first cross-sectional area.

5. The catheter according to claim 3, wherein the second cross-sectional area is in a range of about 25 to about 50% of the first cross-sectional area.

6. The medical device of claim 2, wherein the single common lumen has a third cross-sectional area that is greater than the first cross-sectional area.

7. The medical device of claim 1, wherein the second tubular member forms a distal portion of the first lumen.

8. The medical device of claim 7, wherein the second lumen surrounds the second tubular member proximal to the single common lumen.

9. The medical device of claim 1, wherein the second lumen comprises a restriction.

10. A medical device comprising:
an elongated tubular body having a proximal portion with a proximal end and having a distal portion with a distal end;
a first lumen extending distally from the proximal end of the tubular body, the first lumen having a proximal portion and a distal portion, the proximal portion of the first lumen having a laterally accessible region and the distal portion of the first lumen having a closed region;
a second lumen extending distally from the proximal end of the tubular body, the second lumen having a proximal portion and distal portion, the first and second lumens extending within and along the proximal portion of the elongated catheter body;
a hub assembly adjacent to the proximal portion of the tubular body;
wherein the second lumen is defined along an inner wall surface of the tubular body; and
a restriction disposed within the distal portion of the second lumen and attached to the inner wall surface;
wherein the first lumen and the second lumen form a single common lumen having an open distal end within the distal portion of the tubular body which extends to and through a distal end of the distal portion of the tubular body.

11. The medical device of 10, wherein the proximal portion of the second lumen has a first cross-sectional area and the distal portion of the second lumen at the restriction has a second cross-sectional area.

12. The medical device of claim 11, wherein the second cross-sectional area is smaller than the first cross-sectional area.

13. The medical device of claim 10, wherein the second lumen surrounds first lumen along a length prior to forming the single common lumen.

14. The medical device claim 10, wherein the elongated tubular body comprises a third lumen.

15. The medical device of claim 10, wherein the proximal portion of the tubular body has a first diameter and the distal portion of the tubular body has a second diameter that is smaller than the first diameter.

16. A medical device comprising:
an elongate tubular member having a proximal portion and a distal portion, the elongate tubular member including a first lumen extending distally from the proximal portion and a second lumen extending side-by-side with the first lumen along the proximal portion;
a second tubular member disposed within at least a portion of the first lumen;
a hub assembly adjacent to the proximal portion of the first tubular member; and
a restriction disposed within a distal portion of the second lumen
wherein the first lumen and second lumen form a single common lumen having an open distal end within the distal portion of the elongate tubular member;
wherein a distal region of the second tubular member extends distally from the first lumen and into the single common lumen;
wherein at least a portion of the distal region of the second tubular member and the single common lumen are coaxial; and
wherein the first lumen has a laterally accessible region.

17. The medical device of 16, wherein a proximal portion of the second lumen has a first cross-sectional area and the distal portion of the second lumen at the restriction has a second cross-sectional area.

18. The medical device of claim 17, wherein the second cross-sectional area is smaller than the first cross-sectional area.

* * * * *